United States Patent [19]

Jennings

[11] Patent Number: Plant 6,782

[45] Date of Patent: May 9, 1989

[54] BLACKBERRY PLANT—LOCH NESS CULTIVAR

[75] Inventor: Derek L. Jennings, Dundee, Scotland

[73] Assignee: Scottish Crop Research Institute, Dundee, Scotland

[21] Appl. No.: 125,010

[22] Filed: Nov. 24, 1987

[51] Int. Cl.[4] ..... A01H 5/03

[52] U.S. Cl. ..... Plt./46

[58] Field of Search ..... Plt./46

*Primary Examiner*—Robert E. Bagwill

*Attorney, Agent, or Firm*—Burns, Doane, Swecker & Mathis

[57] ABSTRACT

This cultivar was formed by crossing two unnamed selections bred at the Scottish Crop Research Institute. The new cultivar is noted for its high yield of large, slightly glossy black fruit and its sturdy, erect or semi-erect thornfree stems.

2 Drawing Sheets

SUMMARY OF THE INVENTION

The original plant of the new variety was selected from a family of seedlings resulting from a cross made in 1978 at the Scottish Crop Research Institute (SCRI), Dundee, United Kingdom, between two unnamed blackberry selections of complex parentage, both of which were bred at the SCRI. The pedigree of the LOCH NESS cultivar of the present invention is summarized as follows:

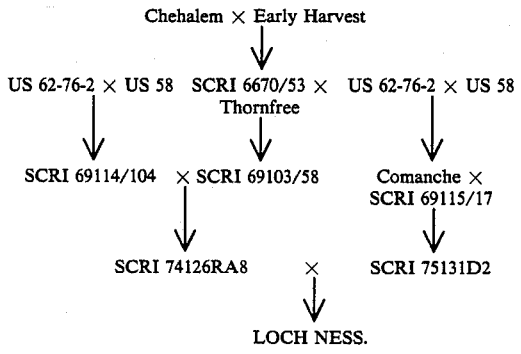

The new cultivar is notable for its large fruit size, hardiness, high yield and earliness of ripening. Its performance has been evaluated at the Scottish Crop Research Institute; the National Fruit Trials at Faversham, England; and in British Columbia, Canada. The variety may be reproduced with ease by leaf-bud cuttings, root cuttings, rooted tips or tissue culture. Continuous asexual propagation has demonstrated that its characteristics are stable and are transmitted without change through succeeding propagations.

BRIEF DESCRIPTION OF THE PHOTOGRAPHS

The accompanying drawings show typical specimens of the new variety in color as nearly true as is reasonably possible to make the same in color illustrations of this character. In each instance the photographs were made at the Scottish Crop Research Institute, Dundee, United Kingdom.

DETAILED DESCRIPTION

Figure 1:
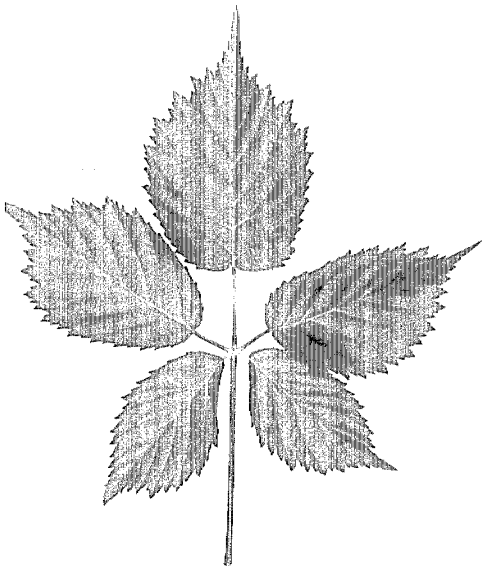
FIG. 1 is a mature leaf from a one-year old stem, photographed in early November 1986, and showing the stalklets which attach the leaflets to the petiole and the leaf serrations and prominent veins.
Figure 2:
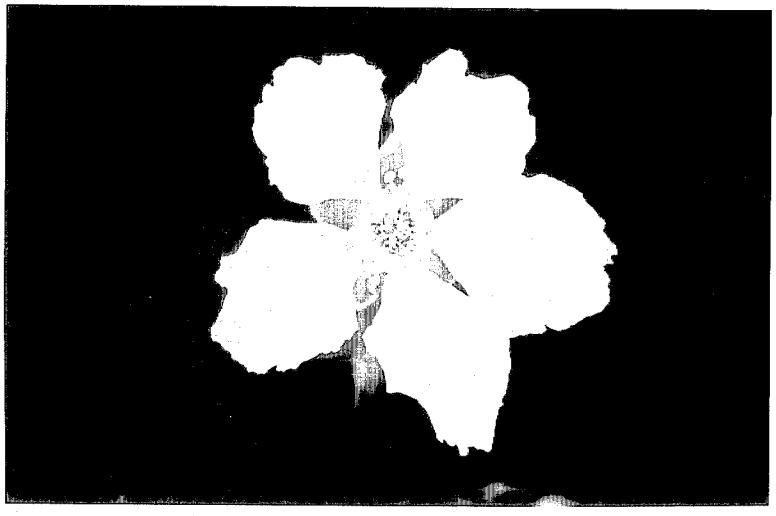
FIG. 2 is an open flow showing the substantially white color of the petals.
Figure 3:
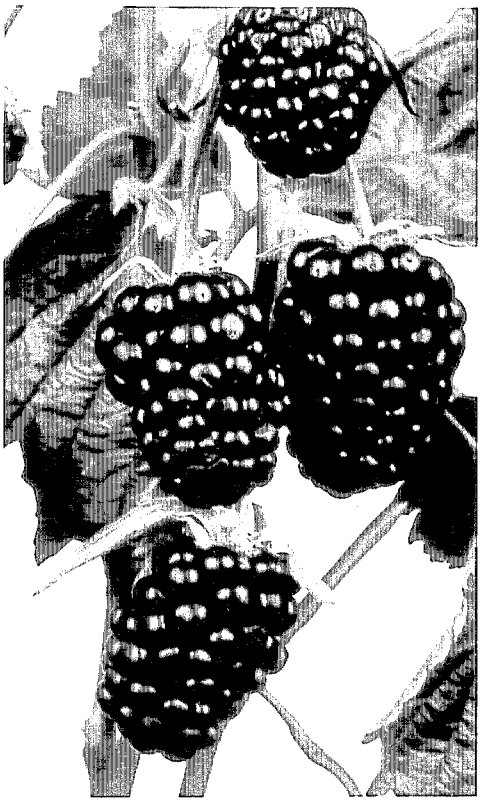
FIG. 3 is a view of four representative fruits photographed during August 1983 wherein the slightly glossy appearance and the blunt-conical shape are apparent.
Figure 4:
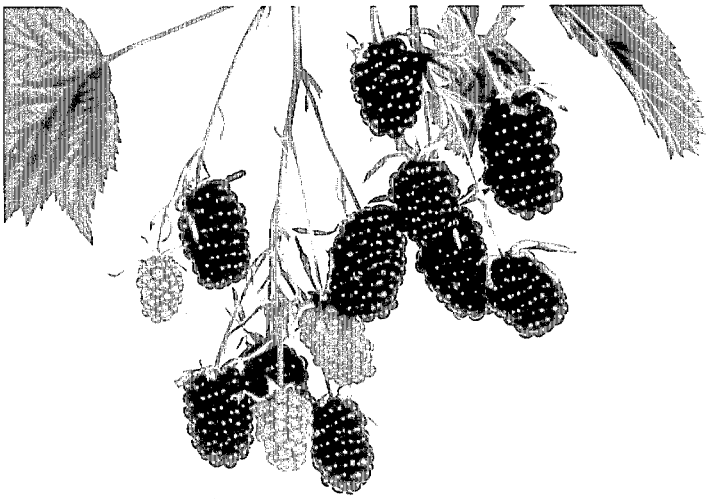
FIG. 4 is a more distant view of a fruiting lateral with ripe fruits photographed during August 1983 showing the characteristics of the fruit and pedicel.

The following is a detailed description of the characteristics of the new variety as observed at the Scottish Crop Research Institute. Color terminology employed is to be accorded its ordinary dictionary significance. As will be apparent to those skilled in horticultural science, the colors of the leaves and stems vary with the stage of growth and are useful only for general guidance. Similarly, the fruit color varies with the stage of ripeness.

DESCRIPTION OF ONE YEAR OLD VEGETATIVE SHOOTS

The new cultivar exhibits vigorous sturdy shoots which are erect during the early part of the season. These become semi-erect as growth proceeds though the tendency to become semi-erect becomes less marked in older established plants. The stems are angular, typically pentangular, thornfree and may be either green or pigmented. The immature tip portion is hairy, but hairs are inconspicuous or absent in sub-terminal parts of the stem. The canes usually become a deep purple in the autumn, but areas of green remain, principally towards the bases of the canes and in unexposed areas. The leaflets are five in number and attached to the petiole by distinct stalklets. The stalklet of the terminal petiole is particularly conspicuous. Established plants commonly produce approximately 5 or more (e.g., 5 to 9) replacement canes from root-stock buds.

General Habit

Strength of growth: Vigorous, sturdy shoots produced in moderate to high numbers. Suckering in the true botanical sense does not occur, but approximately 5 to 9 replacement canes commonly are produced from root-stock buds each year.

Habit of growth: Erect in early part of season, becoming semi-erect later in young plants but only slightly so in mature plants. Branching is common from the lower nodes.

Coloring: Medium green with areas of brownish-purple coloration.

Stem surface: Thornfree, slightly hairy at the stem apices but not in sub-terminal parts and with a weak bloom.

Leaf color: Medium green, red pigments usually present in petiole and leaflet stalks.

Leaf characteristics: There are conspicuous stalklets (petiolae) attaching the five leaflets to the petiole. The stalklet of the terminal leaflet is longest, those of the middle leaflets intermediate and those of the basal leaflets relatively short. The leaf is flat with prominent veins and serrations.

Description of Fruiting Laterals, Flowers and Fruit

White flowers and fruits are well presented on flexible fruiting laterals of medium length (typically approximately one foot in length but are influenced by growing conditions). The fruits are blunt-conical in configuration and large. When fully ripe they are a deep black and slightly glossy with little or no downiness. The flavor is typical of blackberries with slight acidity. The season of ripening depends on the environment, but starts relatively early for a blackberry of this type and extends over a long period.

General Description

Fruiting laterals: Usually approximately one foot in length.

Flower: Medium size with white petals.

Fruit: Large, slightly glossy, black and blunt-conical in shape. Fruit weight is typically approximately 6 grams but ranges up to approximately 10 grams. Fruit dimensions commonly range from approximately 25 to 40 mm. in length (often approximately 28 mm.) and from approximately 20 to 28 mm. in breadth (often approximately 21 mm.).

Fruit quality; Firm with a pleasantly sharp flavor. Excellent storage capability, but there is small tendency for frozen fruit to turn red, especially if not fully mature when picked.

Season of ripening: Extends over a long period and commences to ripen relatively early for a blackberry of this type.

Yield: Fruit yield per plant is influenced considerably by plant spacing and rainfall. For plants spaced three feet apart in rows which are nine feet apart a typical yield is approximately 4.5 Kg. per plant.

Disease and pest susceptibility: Has average susceptibility to common diseases and pests that affect blackberries. No excessive susceptibility has been found.

I claim:

1. A new and distinct variety of blackberry substantially as herein shown and described together with the parts thereof.

* * * * *